United States Patent [19]

Moser et al.

[11] 3,980,798
[45] Sept. 14, 1976

[54] DICHLOROMALEIC IMIDES FOR FUNGICIDAL COMPOSITION AND METHOD

[75] Inventors: Hans Moser, Magden, AG; Elmar Sturm, Aesch; Raphael Menassé, Basel, all of Switzerland

[73] Assignee: Ciba-Geigy Corporation, Ardsley, N.Y.

[22] Filed: Apr. 17, 1975

[21] Appl. No.: 568,946

Related U.S. Application Data

[62] Division of Ser. No. 321,624, Jan. 8, 1973, Pat. No. 3,894,043.

[30] Foreign Application Priority Data

Jan. 12, 1972  Switzerland............................ 438/72
Dec. 4, 1972  Switzerland........................ 17626/72

[52] U.S. Cl. ............................................... 424/274
[51] Int. Cl.² .......................................... A01N 9/22
[58] Field of Search ............. 424/274; 260/326.5 S, 260/326.5 FM

[56] References Cited
UNITED STATES PATENTS
2,962,504  11/1960  Walker et al. ................... 260/326.5

FOREIGN PATENTS OR APPLICATIONS
1,145,583  3/1969  United Kingdom.............. 260/326.5

*Primary Examiner*—V. D. Turner
*Assistant Examiner*—D. W. Robinson
*Attorney, Agent, or Firm*—Harry Falber; Frederick H. Rabin

[57] ABSTRACT

Fungicidal composition and method utilizing, as the active ingredient, imides of the formula

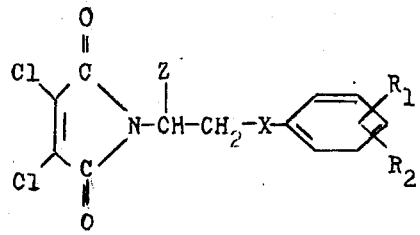

wherein Z represents hydrogen or methyl, X represents oxygen, sulphur or the group $NR_3$, in which $R_3$ represents hydrogen or methyl, $R_1$ represents hydrogen, chlorine, bromine or trifluoromethyl, and $R_2$ represents hydrogen, halogen, methyl or trifluoromethyl.

13 Claims, No Drawings

DICHLOROMALEIC IMIDES FOR FUNGICIDAL COMPOSITION AND METHOD

This is a division of application Ser. No. 321,624, filed on Jan. 8, 1973, now U.S. Pat. No. 3,894,043.

The present invention relates to new dichloromaleic imides, their manufacture and use in pest control.

The dichloromaleic imides have the formula

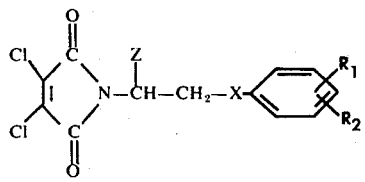
(I)

wherein Z represents hydrogen or methyl, X represents oxygen, sulphur or the group $NR_3$, in which $R_3$ represents hydrogen or methyl, $R_1$ represents hydrogen, chlorine, bromine or trifluoromethyl, and $R_2$ represents hydrogen, halogen, methyl or trifluoromethyl.

By halogen is meant fluorine, chlorine, bromine or iodine, but in particular chlorine or bromine.

Preferred compounds on account of their action are those of the formula

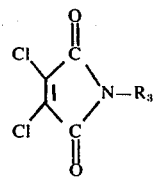
(II)

wherein $R_3$ represents

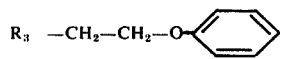

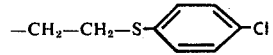

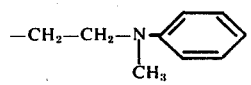

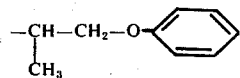

or

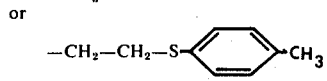

The active substances of the formula I can be manufactured by known methods which are described in the literature, for example by reacting the compound of the formula

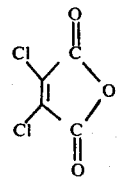
(III)

with a compound of the formula

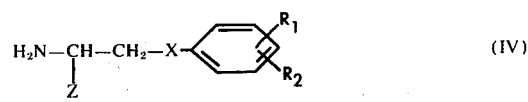
(IV)

wherein X, Z, $R_1$ and $R_2$ have the meanings given for the formula I, in the presence of acids at elevated temperature, preferably in acetic or hydrochloric acid, e.g. 6n hydrochloric acid, at a temperature between 80°–120°C.

The starting materials of the formulae III and IV are known compounds, the processes for the manufacture of which are described in the literature.

The compounds of the formula I have a broad biocidal activity spectrum and can be used for combating various plant and animal pests. The activity of these compounds is good against representatives of the division Thallophyta, chiefly against plant pathogenic fungi, especially leaf fungi, for example on cereals, rice, vegetables, vines, fruit and other cultures, from the series Oomycetes, Moniliales, Uredinales, Erysiphales, Sphaeropsidales, e.g. *Botrytis cinerea*, *Piricularia oryzae*, *Podosphaera leutoricha*, *Uromyces appendiculatus*, *Plasmopara viticola*, *Septoria agricola*, *Puccinia triticina*.

The active substances according to the invention are also active against fungi which attack the plants from the soil and partially cause tracheomycosis, and also those which damage seeds present in the soil.

The fungicidal action of the compounds of the formula I can be substantially broadened and adapted to the given circumstances by the addition of other fungicides. The following compounds, for example, are suitable additives:

elementary sulphur
ammonium polysulphide and metal polysulphides
boric acid and borates
nickel sulphate
potassium chromate
copper (I) oxide (KUPFEROXID)
Bordeaux broth and further inorganic and organic copper salts
bis-(tri-n-butyl tin)oxide
triphenyl tin hydroxide (FENTINHYDROXID)
triphenyl tin acetate (FENTINACETAT) and further organic tin compounds
methyl mercury-8-hydroxyquinolate (Ortho LM)
N-(methyl mercury)-1,4,5,6,7,7-hexachlorobicyclo[2.2.1]hept-5-ene-2,3-dicarboximide
N-(ethylmercury)-1,4,5,6,7,7,-hexachlorobicyclo[2.2.1]hept-5-ene-2,3-dicarboximide
N-(ethyl mercury)-p-toluenesulphonic anilide
phenyl mercury acetate (PMA)
phenyl mercury urea
mixture of ethyl mercury-2,3-dihydroxypropyl mercaptide and ethyl mercury acetate and further inorganic and organic mercury compounds
O,O-diethyl-phthalimidiphosphonothioate 5-amino-bis-(dimethylamido)phosphinyl-3-phenyl-1,2,4-triazole (TRIAMIPHOS)
5-methylamino-bis-(dimethylamido)-phosphinyl-3-phenyl-1,2,4-triazole
O,O-diethyl-O-2-pyrazinyl-phosphorus thioate
O-ethyl-S,S-diphenyl-dithiolphosphate
O-ethyl-S-benzyl-phenyldithiophosphonate
O,O-diisopropyl-S-benzyl-phenyldithiophosphonate
O,O-diethyl-S-benzyl-thiophosphate
O-butyl-S-ethyl-S-benzyl-dithiolphosphate
O-pentachlorophenyl-bis-(dimethylamido)-phosphate
O-ethyl-S-benzyl-phenyl-phosphonate
diethylamido-benzenethiophosphonic-2-methyl-imidazolide
methylbromide
methyl isocyanate
1,3-dichloropropene and related halogenated $C_3$ and $C_4$ hydrocarbons
1-chloro-2-nitro-propane
2-chloro-1-nitropropane
dichlorotetrafluoroacetone
sorbic acid and its potassium salts
dodecylguanidine acetate (dodine)
dodecylguanidine phthalate
acetylene dicarboxylic diamide
1,2-dicyano-1,2-dichloroethylene
1,2-dichloro-1-(methylsulphonyl)ethylene
1,2-dichloro-1-(butylsulphonyl)ethylene
trans-1,2-bis-(n-propylsulphonyl)ethylene
bis-(1,2-trichloroethyl)sulphoxide
bis-(n-propyl-chlorodifluoromethylthio)-sulphone diamide
p-dichlorobenzene
hexachlorobenzene (HCB)
1,2,4-tetrachloro-4-nitrobenzene(TECNACEN)
pentachloronitrobenzene (QUINTAZEN)
isomer mixture of 1,3,4-trichloro-2,6-dinitrobenzene and 1,2,3-trichloro-4,6-dinitrobenzene
2,4,5,6-tetrachloroisophthalic nitrile
2,4-dinitrophenyl-thiocyanate
diphenyl
O-nitrodiphenyl
1-chloro-2,4-dinitronaphthalene
2,4,6-trichlorophenyl
2,4,5-trichlorophenyl-chloroacetate
trichlorophenol, zinc salt
m-cresyl acetate
2,3,4,6-tetrachlorophenol
pentachlorophenol (PCP)
O-dihydroxybenzene
2,4-dioxy-n-hexylbenzene
2-phenylphenol
3,5-dibromosalicylaldehyde
2-benzyl-4-chlorophenol
2,2'-dihydroxy-5,5'-dichloro-diphenylmethane (DICHLORPHEN)
2,2'-dihydroxy-3,3',5,',6,6'-hexachloro-diphenylmethane
2,2'-dihydroxy-5,5'-dichloro-diphenylsulphide
2,2'-dihydroxy-3,3',5,5'-tetrachloro-diphenylsulphide
disodium-2,2'-dihydroxy-3,3',5,5'-tetrachloro-diphenylsulphide
4-chloro-o-phenylphenol
1,4-dichloro-2,5-dimethoxybenzene (CHLORNEB)
salicylanilide
1,2-bis-(3-methoxycarbonyl-2-thiourea)-benzene
1,2-bis-(3-ethoxycarbonyl-2-thiourea)-benzene
(3,5-dimethyl-4-chlorophenoxy)-ethanol
1,4-dichloro-2,5-dimethoxybenzene
2,4,5-trichlorophenylsulphonylmethylthiocyanate
phenylmercapto-methanesulphonamide
2-(1-methyl-n-propyl)-4,6-dinitrophenyl-2-methylcrotonate (BINAPACRYL)
2-(1-methyl-n-propyl)4,6-dinitrophenylisopropylcarbonate (DINOEUTON)
2-(1-methyl-n-heptyl)-4,6-dinitrophenylcrotonate (DINOCAP)
methyl-2,6-dinitro-4-(1-ethyl-hexyl)phenylcarbonate
+
methyl-2,6-dinitro-4(1-propyl-pentyl)phenylcarbonate (DINOCTON)
4-nonyl-2,6-dinitro-phenylbutyrate
S-methyl-2-(1-methyl-n-heptyl)-4,6-dinitrophenylthiocarbonate
1-(3,4-dichloroanilino)-1-formylamino-2,2,2-trichloroethane
2,6-dichloro-4-nitroaniliene (DICHLORAN)
2-cyanoethyl-N-phenylcarbamate
propynyl-N-phenylcarbamate
2-methyl-benzoic anilide
2-iodo-benzoic anilide
2-chloro-benzoic anilide
2,3,5,6-tetrachloro-benzoquinone (1,4) (CHLORANIL)
2,3-dichloro-naphthoquinone(1,4) (DICHLON)
2-amino-3-chloro-naphthoquinone (1.4)
2-chloro-3-acetamino-naphthoquinone(1,4)
4-methyl-2,3,5,10-tetrahydro-3,5,10-trioxo-4H4-H-naphtho(2,3,-b) -1,4-thiazine
quinoximbenzoylhydrazone (BENQUINOX)
N-(trichloromethylthio)phthalimide (FOLPET)
N-(trichloromethylthio)cyclohex-4ene-1,2-dicarboximide (CAPTAN)
N-(1,1,2,2-tetrachloroethylthio)cyclohex-4-ene-1,2-dicarboximide (CAPTAFOL)
N-(1,1,2,2-tetrachloroethylthio)cyclohex-4-ene-1,2-dicarboximide
N'-dichlorofluoromethylthio-NN-dimethyl-N'-phenylsulphamide (DICHLOFLUANIDE)
S-(2-pyridyl-1-oxide)-S'-trichloromethyl-disulphide:-hydrochloride
sodium-N-methyl-dithiocarbamate (METHAM)
sodium-N,N-dimethyl-dithiocarbamate (DDC)
zinc-N,N-dimethyl-dithiocarbamate (ZIRAM)
iron-N,N-dimethyl-dithiocarbamate (FERBAM)
disodium-ethylene-1,2-bis-dithiocarbamate (NABAM)
zinc-ethylene-1,2-bis-dithiocarbamate (ZINEB)
manganese (II)-ethylene 1,2-bis-dithiocarbamate (MANEB)
zinc-propylene-1,2-bis-dithiocarbamate (MEZINEB) (PROPINEB)
complex consisting of (MANEB) and zinc (MANCOZEB)
tetramethylthiuramdisulphide (THIRAM)
complex consisting of (ZINEB) and polyethylene thiruamdisulphide (METIRAM)
bis-(3,4-dichloro-2(5)-furanoyl)ether (mucochloric anhydride)
2-methoxymethyl-5-nitrofuran
5-nitro-furfuradoxime-(2)
5-nitro-furfuryl-amidoxime-(2)
1-oxy-3-acetyl-6-methyl-cyclohexene-(5)-dione(2,4) (dehydroacetic acid)
4,5,6,7-tetrachlorophthalide
3-[2-(3,5-dimethyl-2-oxycyclohexyl)-2-hydroxyethyl]-glutarimide (cycloheximide)

phthalimide
pyridine-2-thiol-1-oxide and 1-hydroxypyridine-2-thione
α,α-bis(4-chlorophenyl)-3-pyridine-methanol (PARINOL)
8-hydroxyquinoline (3-QUINOLINOL)
8-hydroxyquinoline-sulphate (CHINOSOL)
benzoyl-8-hydroxyquinoline-salicylate
6-ethoxy-1,2-dihydro-2,2,4-trimethylquinoline (ETHOXYQUIN)
N-lauryl-isoquinolinium bromide
9-(p-n-hexyloxyphenyl)-10-methyl-acridinium chloride
2-n-heptadecylimidazoline acetate (GLYODIN)
1-hydroxyethyl-2-heptadecylimidazoline
1-phenyl-3,5-dimethyl-4-nitrosopyrazole
1-p-chlorophenyl-3,5-dimethyl-4-nitrosopyrazole
N-(1-phenyl-2-nitropropyl)piperazine
N,N'-bis[1-formamido-2,2,2-trichloroethyl]-piperazine
2-dimethylamino-6-methyl-5-n-butyl-4-hydroxypyrimidine
N-dodecyl-1,4,5,6-tetrahydropyrimidine
N-dodecyl-2-methyl-1,4,5,6-tetrahydroxypyrimidine
2-n-heptadecyltetrahydropyrimidine
1-(4-amino-4-propyl-5-pyrimidyl-methyl)-2-methylpyridiniumchloride hydrochloride
2-(2'-furyl)-benzimidazole (FUBERIDAZOL)
3-dodecyl-1-methyl-2-phenylbenzimidazolium ferricyanide
methyl-n-benzimidazol- 2-yl-N-(butylcarbamoyl)carbamate (BENOMYL)
methyl-n-benzimidazol-2-(O-chloranilino)-4,6-dichloro-sym.-triazine
2-ethylamino-6-methyl-5-n-butyl-4-hydroxypyrimidine
2,6-dichloro-3,5-dicyano-4-phenylpyridine
α-(2,4-dichlorophenyl)-α-phenyl-5-pyrimidine-methynol
5-chloro-4-phenyl-1,2-dithiol-3-one
2,3-dicyano-1,4-dithia-anthraquinone (DITHIANON)
2-(4-thiazolyl)-benzimidazole
4-(2-chlorophenylhydrazono)-3-methyl-5-isoxazolone (DRAZOXOLON)
thiazolidinone-4-thione(2) (RHODANIN)
3-(p-chlorophenyl)-5-methylrhodanine
3,5-dimethyltetrahydro-1-3,5-thiadiazine-β-thione (DAZOMET)
3,3'-acetylene-bis-(tetrahydro-4,6-dimethyl)-2H-1,3,5-thiadiazine-2-thione) (MILNEB)
3-benzylidene-amino-4-phenylthiazoline-2-thione
6-chlorobenzthiazole-2-thiole, zinc salt
6-β-diethylamino-ethoxy-2-dimethylamino-benzthiazole-dihydrochloride
monoethanolammonium-benzthiazole-2-thiole
laurylpyridinium-5-chloro-2-mercaptobenzthiazole
6-(β-diethylaminoethoxy)-2-dimethylaminobenzthiazole-dihydrochloride
3-trichloromethylthiobenzothiazolone
3-trichloromethylthiobenzoxazolone
3-(trichloromethyl)-5-ethoxy-1,2,4-thiadiazole
6-methyl-2-oxo-1,3-dithiolo[4,5-b]-quinoxaline (QUINOMETHIONAT)
2-thio-1,3-dithiolo[4,5-b]-quinoxaline (THIOQUINOX)
2,3-dihydro-5-carboxanilido-6-methyl-1,4-oxathiine
2,3-dihydro-5-carboxanilido-6-methyl-1,4-oxathiine-4,4-dioxide
2,3-dihydro-5-carbox-O-diphenylamido-6-methyl-1,4-oxathiine
N-cyclododecyl-2,6-dimethylmorpholine acetate
N-tridecyl-2,6-dimethylmorpholine
3-(3',5'-dichlorophenyl)-5,5-dimethyloxazolidine-2,4-dione
cetyl-trimethylammonium bromide
n-alkyl($C_{12},C_{14},C_{16}$)dimethylbenzylammonium chloride
dialkyldimethylammonium bromide
alkyldimethylbenzylammonium chloride
alkyl $C_9$-$C_{15}$ tolylmethyltrimethylammonium chloride
p-di-isobutylphenoxyethoxyethyldimethylbenzylammonium chloride
gliotoxin
2,4-diguanidino-3,5-6-trihydroxycyclohexyl-5-deoxy-2-O-(2-deoxy-2-methylamino-α-L-glucopyranoxyl)3-C-formyl-β-L-lyxopentano-furanoside (STREPTOMYCIN)
7-chloro-4,6-dimethoxycumaran-3-one-2-spiro-1'-(2'-methoxy-6'-methylcyclohex-2'-ene-4'-one (GRISEOFULVIN)
4-dimethylamino-1,4,4a,5,5a,6,11,12a-octahydro-3,5,6,10,12,12a-hexahydroxy-6-methyl-1,11-dioxo-2-naphthacene-carboximide (OXYTETRACYCLIN)
7-chloro-4-dimethylamino-1,4,4a,5,5a,6,11,12a-octahydro-3,6,10,12,12a-pentahydroxy-6-methyl-1,11-dioxo-2-naphthacene-carboximide (CHLORTETRACYCLIN)
(PIMARCIN)
(LANCOMYCIN)
(PHLEOMYCIN)
(KASUGAMYCIN)
(PHYTOACTIN)
D(-)-threo-2,2-dichloro-N-3-hydroxy-a-(hydroxymethyl)-p-nitrophen-ethyl-acetamide (CHLORAMPHENICOL)
blasticidin-S-methyl-benzylamino-benzenesulphonate
N-(3,5-dichlorophenyl)-succinimide
N-(3,5-dichlorophenyl)-itaconimide
N-(3-nitrophenyl)-itaconimide
phenoxyacetic acid
sodium-p-dimethylamino-benzenediazosulphonate
acrolein-phenylhydrazone
2-chloroacetaldehyde-(2,4-dinitrophenyl)-hydrazone
2-chloro-3-(tolysulphonyl)-propionitrile
1-chloro-2-phenyl-pentane-diol(4,5)-thione(3)
p-nonylphenoxypolyethyleneoxyethanol iodine complex
(α-nitromethyl)-O-chlorobenzythioethylamine hydrochloride
3-(p.-t.-butyl-phenylsulphonyl)-acrylonitrile
octachlorocyclohexenone
pentachlorobenzyl alcohol
pentachlorobenzyl acetate
pentachlorobenzaldehyde cyanohydrin
2-norcamphane-methanol
2,6-bis-(dimethylaminoethyl)-cyclohexanone
decachloro-octahydro-1,3,4-metheno-2H-cyclobuta[cd]pentalen-2-one
1-(3-chloroallyl)-3,5,7-triaza-1-azonia-admantane chloride.

The compounds of the formula I can be used in plant protection as pure active substance or together with suitable carriers and/or additives. Suitable carriers and additives can be solid or liquid and correspond to the substances conventionally used in formulation technology, for example, natural or regenerated mineral substances, solvents, dispersants, wetting agents, adhesives, thickeners, binders or fertilisers.

The agents according to the invention are manufactured in known manner by intimately mixing and/or grinding active substances of the formula II with the suitable carriers, optionally with the addition of dispersants or solvents which are inert towards the active substances. The active substances may be available and can be used in the following forms:

Solid forms:
Dusts, tracking agents, granules, coated granules, impregnated granules and homogeneous granules.

Liquid forms:
a. active substances which are dispersible in water: wettable powders, pasts, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaccous, earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, nutshell meal, cellulose powder, residues of plant extractions, activated charcoal etc. These substances can either be used alone or in admixture with one anotzer.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivates (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be deluted with water to any concentration desired. They consist of active substance, carrier, optionally additives which stabilize the active substance, surface-active substance and anti-foam agents and, optionally, solvents.

Wettable powder and pastes are obtained by mixing and grinding the active substances with dispersing agents and pulverulent carriers in suitable apparatur until homogeneity is attained. Carriers are, for example, those mentioned for the solid forms of appliaction. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and formaldehyde, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfated hexadecanlos, heptadecanols, octadecanols, and salts of sulfated fatty alcohol glycol ethers, the sodium salt of oleoyl ethionate, the sodium salt of oleoyl methyl tauride, ditertiary acetylene glycols, dialkal dilauryl ammonium chloride and fatty acid alkali and alkaline earth metal salts.

Suitable anti-foam agents are silicones.

The active substances are mixed, ground sieved and strained with the additives mentioned above that, in wettable powder, the solid particle size of from 0.02 to 0.04 and in pasts; of 0.03 is not exceeded. To produce emulsifiable concentrates and pastes, dispersing agents such as those cited above, organic solvents and water are used, Examples of suitable solvents are the following: alcohols, benzene, xylene, toluene, dimethyl sulfoxide, and mineral oil fractions boiling between 120° and 350°C. The solvents must be practically odorless, not phytotoxic, inert to the active substances and not readely inflammable.

Furthermore, the agents according to the invention can be applied in the form of solutions. For this purpose the active substance or several active substances of the general formula I are dissolved, in suitable organic solvents, mixtures of solvents or in water. Aliphatic and aromatic hydrocarbons, chlorinated derivatives thereof, alkyl naphthalenes, and mineral oils alone or mixed with each other, can be used as organic solvents.

The content of active substance in the above described agents is between 0.1% to 95%, in which connection it should be mentioned that in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust.

| (a) | 5 parts of active substance |
| | 95 parts of talcum |
| (b) | 2 parts of active substance |
| | 1 part of higly disperse silica |
| | 97 parts of talcum. |

The active substances are mixed with the carriers and ground.

Granules

The following substances are used to produce 5% granules:

| 5 | parts of active substance, |
| 0.25 | parts of epichlorohydrin, |
| 0.25 | parts of cetyl polyglycol ether, |
| 3.50 | parts of polyethylene glycol, |
| 91 | parts of kaolin (particle size 0.2–0.8 mm). |

The active substance is mixed with epichlorohydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder:

The following constituents are used for the preparation of (a) a 40%, (b) and (c) a 25%, and (d) a 10% wettable powder:

| (a) | 40 | parts of active substance, |
| | 5 | parts of sodium lignin sulphonate, |
| | 1 | part of sodium dibutyl-naphthalene sulphonate, |
| | 54 | parts of silica acid. |
| (b) | 25 | parts of active substance, |
| | 4.5 | parts of calcium lignin sulphonate, |
| | 1.9 | parts of Champagne chalk/hydroxyethyl cellulose mixture (1:1), |
| | 1.5 | parts of sodium dibutyl naphthalene sulphonate, |
| | 19.5 | parts of silica acid, |
| | 19.5 | parts of Champagne chalk, |
| | 28.1 | parts of kaolin. |
| (c) | 25 | parts of active substance, |
| | 2.5 | parts of isooctylphenoxy-polyoxy-ethylene-ethanol, |
| | 1.7 | parts of Champagne chalk/hydroxyethyl cellulose mixture (1:1), |
| | 8.3 | parts of sodium aluminium silicate, |
| | 16.5 | parts of kieselguhr, |
| | 46 | parts of kaolin, |
| (d) | 10 | parts of active substance, |
| | 3 | parts of a mixture of the sodium salts of saturated fatty alcohol sulphates, |
| | 5 | parts of naphthalenesulphonic acid/formalehyde condensate, |
| | 82 | parts of kaolin. |

The active substances are intimately mixed, in suitable mixers, with the additives, the mixture being then ground in the appropriate mills and rollers. Wettable power are obtained which can be diluted with water to give suspensions of any desired concentration.

Emulsifiable concentrates:

The following substances are used to produce (a) a 10% and (b) a 25% emulsifiable concentrate:

| (a) | 10 | parts of active substance, |
| | 3.4 | parts of epoxidised vegetable oil, |
| | 13.4 | parts of a combination emulsifier consisting of fatty alcohol polyglycol ether and alkylarylsulphonate calcium salt, |
| | 40 | parts of dimethylformamide, |
| | 43.2 | parts of xylene. |
| (b) | 25 | parts of active substance, |
| | 2.5 | parts of epoxidised vegetable oil, |
| | 10 | parts of an alkylarylsulphonate/fatty alcohol-polyglycol ether mixture, |
| | 5 | parts of dimethylformamide, |
| | 57.5 | parts of xylene. |

From these concentrates it is possible to produce, by dilution with water, emulsions of any desired concentration.

Spray:

The following constituents are used to prepare a 5% spray:

| 5 parts of active substance, |
| 1 part of epichlorohydrin, |
| 94 parts of benzine (boiling limits 160°– 190°C). |

EXAMPLE 1

Manufacture of N-[2-(4'-tolylmercapto)ethyl]-3,4-dichloromaleic imide

To a solution of 108 g of dichloromaleic anhydride in 300 ml of glacial acetic acid are added 87 g of 2-(4'-tolylmercapto)ethylamine, in the course of which the temperature rises to 60°C. The mixture is stirred for 2 hours at 100°C and the precipitated yellowish crystals are then filtered with suction, to yield 120 g of N-(4'-tolylmercaptoethyl)-3,4-dichloromaleic imide (m.p. 98°–91°C).

The following compounds are also manufactured in analogous manner:

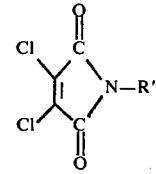

| R' | m.p. °C |
|---|---|
| —CH$_2$—CH$_2$—S—⟨phenyl⟩ | 93–95 |
| —CH$_2$—CH$_2$—O—⟨phenyl⟩ | 88–90 |
| —CH$_2$—CH$_2$—O—⟨phenyl⟩—CH$_3$ | 79–81 |
| —CH$_2$—CH$_2$—N(CH$_3$)—⟨phenyl⟩ | 112–114 |
| —CH$_2$—CH$_2$—NH—⟨phenyl⟩ | 137–139 |

-continued

| R' | m.p. °C |
|---|---|
| —CH$_2$—CH$_2$—S—C$_6$H$_4$—Cl | 95–97 |
| —CH(CH$_3$)—CH$_2$—O—C$_6$H$_5$ | 66–68 |
| —CH$_2$—CH$_2$—O—C$_6$H$_3$Cl$_2$ (2,4-Cl) | |
| —CH$_2$—CH$_2$—NH—C$_6$H$_4$—CH$_3$ | |
| —CH$_2$—CH$_2$—NH—C$_6$H$_3$Cl$_2$ | |
| —CH$_2$—CH$_2$—NH—C$_6$H$_3$(CH$_3$)$_2$ | |
| —CH$_2$—CH$_2$—S—C$_6$H$_4$—CH$_3$ | |
| —CH$_2$—CH$_2$—S—C$_6$H$_4$—CH$_3$ | |

EXAMPLE 2

Action against *Botrytis cinerea* on *Vicia faba*

Fully developed, uniformly large leaves of *Vicia faba*, which have been sprayed dripping wet from a spraying device with a broth (0.1% content of active substance) prepared from an active substance formulated as a 10% wettable powder, were placed three at a time in Petri dishes lined with filter paper. When the leaves were dry again, they were infected with a freshly prepared, standardised spore suspension of the fungus (concentration: 100'000 spores/ml) and kept for 48 hours in a humid atmosphere at 20°C. After this time, the leaves displayed black, initially dot-shaped specks which rapidly spread. The number and size of the infected areas served as a yardstick for determining the effectiveness of the test substance.

The compounds of the formula I showed good action in the above test against *Botrytis cinerea*.

EXAMPLE 3

Action against *Uromyces appendiculates* on *Phaseolus vulgaris*

*Phaseolus vulgaris* plants in the 2-leaf stage were sprayed until dripping wet with a suspension of the active substance formulated as wettable powder (concentration = 0.1% of active substance). After the spray coating had dried, the plants were infected with a fresh spore suspension of bean rust and then kept for 1 day in a humid chamber, then for 12 days in a green-house at 20°–22°C.

The number and size of the rust pustules served as a yardstick for assessing the effectiveness of the active substances.

The compounds according to Example 1 showed good action in the above test against *Uromyces appendiculatus*.

EXAMPLE 4

Action against *Podosphaera leucotricha* (Ell. et Ev.) Salm. on young apple trees Apple tree cuttings of the type MM III were reared in a greenhouse at 20°C and 90% relative humidity throughout the duration of the test. When 3 to 4 leaves had formed on each of the developing lateral shoots, these leaves were sprayed dripping wet with a broth (0.1% content of active substance) prepared from the active substance formulated as 10% wettable powder. After the coating layer had dried, the leaves were uniformly sprayed on the topside with a spore suspension of the fungus.

The trees were sprayed again with the above described active substance preparation 7 – 14 days after the first treatment. The test was evaluated 12 days after the final treatment.

The number and size of the infected areas served as a yardstick for evaluating the effectiveness of the test substance.

The compounds according to Example 1 showed good action in the above test against *Podosphaera leucotricha*(Ell.et Ev.)Salm.

EXAMPLE 5

Action against *Plasmopara viticola* (Bert. et Curt.) (Berl. et De Toni) on vines Vine cuttings of the variety "Chasselas" were reared in a greenhouse. Three plants in the 10-leaf stage were sprayed dripping wet with a broth (0.1% active substance content) prepared from the active substance formulated as a 10% wettable powder. After the coating layer had dried, the plants were uniformly infected on the underside of the leaves with the spore suspension of the fungus. The plants were subsequently kept for 8 days in a humid chamber, after which time the symtoms of disease became visible on the control plants. The number and size of the infected areas served as a yardstick for evaluating the effectiveness of the active substance.

The compounds according to Example 1 showed good action in the above test against *Plasmopara viticola* (Bert.et Curt.) (Berl. et De Toni).

EXAMPLE 6

Action against *Septoria agricola* Spegazzini on celery plants

Celery plants of the variety "Challon" were reared in a greenhouse. 15 centimeter high plants were each sprayed dripping wet with a broth (0.1% content of active substance) prepared from the active substance formulated as 10% wettable powder. After the coating layer had dried, the plants were infected with a spore suspension of the fungus. Symptoms of disease occured after 2 days in a humid chamber and 12 days at 20°–22°C and 90% relative humidity in a greenhouse. The number and size of the infected areas served as a yardstick for evaluating the effectiveness of the test substance.

The compounds according to Example 1 showed good action in the above test against Septoria agricola Spegazzini.

EXAMPLE 7

Action against *Puccinia triticina* Erites on Triticum

In a greenhouse at 20°C young wheat plants app. 10 cm in length were sprayed dripping wet with a broth (0.1% content of active substance) prepared from the active substance formulated as a 10% wettable powder. When the coating layer had dried, the plants were uniformly infected with a uredospore suspension of the fungus. Evaluation took place after 5 days in a humid chamber and 12 days in a greenhouse at 20°–22°C and normal relative humidity. The number and size of the infected areas served as a yardstick for evaluating the effectiveness of the test substance.

The compounds according to Example 1 showed good action in the above test against Puccinia triticina Eritess.

EXAMPLE 8

Action against *Piricularia Oryzae* Bri. et Cav. on rice

Rice plants were reared in a greenhouse and sprayed once prophylactically with an aqueous spray broth containing 0.1% active substance. Two days later, the 10 treated plants were infected with exospores of *Piricularia oryzae* Bri. et Cav. and examined for attack by fungus after 5 days incubation in a humid chamber.

The compounds according to Example 1 showed good action in the above test against *Piricularia oryzae*.

We claim:

1. A fungicidal composition which comprises a fungicidally effective amount of a compound of the formula

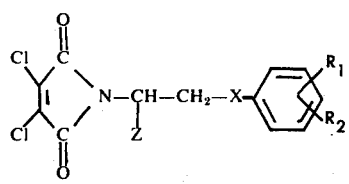

wherein Z represents hydrogen or methyl, X represents oxygen, sulphur or the group $NR_3$, in which $R_3$ represents hydrogen or methyl, $R_1$ represents hydrogen, chlorine, bromine or trifluoromethyl, and $R_2$ represents hydrogen, halogen, methyl or trifluoromethyl, together with a suitable inert carrier therefor.

2. The fungicidal composition of claim 1, wherein said compound is

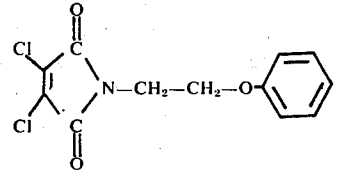

3. The fungicidal composition of claim 1, wherein said compound is

Cl\C(=O)\C(Cl)/C(=O)—N—CH₂—CH₂—S—⟨C₆H₄⟩—CH₃

4. The fungicidal composition of claim 1, wherein said compound is

Cl\C(=O)\C(Cl)/C(=O)—N—CH₂—CH₂—S—⟨C₆H₄⟩—Cl

5. The fungicidal composition of claim 1, wherein said compound is

Cl\C(=O)\C(Cl)/C(=O)—N—CH₂—CH₂—N(CH₃)—⟨C₆H₅⟩

6. The fungicidal composition of claim 1, wherein said compound is

Cl\C(=O)\C(Cl)/C(=O)—N—CH(CH₃)—CH₂—O—⟨C₆H₅⟩

7. A method for the control of fungi which comprises applying to the locus thereof, a fungicidally effective amount of a compound of the formula Cl\C(=O)\C(Cl)/C(=O)—N—CH(Z)—CH₂—X—⟨C₆H₃R₁R₂⟩ wherein Z represents hydrogen or methyl, X represents oxygen, sulphur or the group $NR_3$, in which $R_3$ represents hydrogen or methyl, $R_1$ represents hydrogen, chlorine, bromine or trifluoromethyl, and $R_2$ represents hydrogen, halogen, methyl or trifluoromethyl.

8. The method of claim 7, wherein said compound is

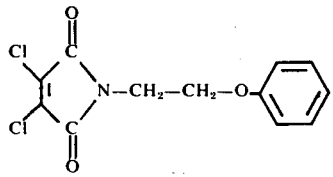

9. The method of claim 7, wherein said compound is

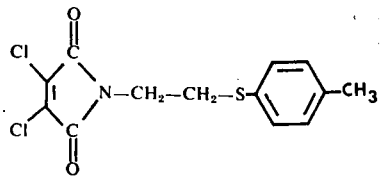

10. The method of claim 7, wherein said compound is

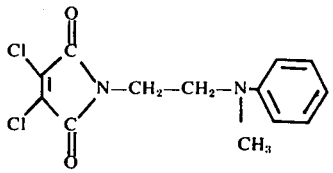

11. The method of claim 7, wherein said compound is

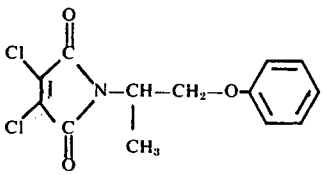

12. The method of claim 7, wherein said compound is

13. A method according to claim 7, wherein plant pathogenic fungi are combated.

* * * * *